(12) United States Patent
Kurt et al.

(10) Patent No.: US 11,033,247 B2
(45) Date of Patent: Jun. 15, 2021

(54) ULTRASOUND SYSTEM AND METHOD OF PROVIDING GUIDE FOR IMPROVED HPRF DOPPLER IMAGE

(71) Applicant: SAMSUNG MEDISON CO., LTD., Gangwon-do (KR)

(72) Inventors: Sandstrom Kurt, Gangwon-do (KR); Dae-young Kim, Gangwon-do (KR); Tae-yun Kim, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 1228 days.

(21) Appl. No.: 15/011,077

(22) Filed: Jan. 29, 2016

(65) Prior Publication Data
US 2016/0220227 A1    Aug. 4, 2016

(30) Foreign Application Priority Data

Jan. 30, 2015    (KR) .......................... 10-2015-0015580

(51) Int. Cl.
*A61B 8/14*    (2006.01)
*A61B 8/00*    (2006.01)
(Continued)

(52) U.S. Cl.
CPC ................. *A61B 8/14* (2013.01); *A61B 8/06* (2013.01); *A61B 8/461* (2013.01); *A61B 8/467* (2013.01); *A61B 8/488* (2013.01); *A61B 8/5207* (2013.01); *A61B 8/5269* (2013.01); *G01S 7/5202* (2013.01); *G01S 7/52076* (2013.01);
(Continued)

(58) Field of Classification Search
None
See application file for complete search history.

(56) References Cited

U.S. PATENT DOCUMENTS

| 4,817,618 A | 4/1989 | DesJardins et al. |
| 5,564,424 A | 10/1996 | Yao |
| (Continued) | | |

FOREIGN PATENT DOCUMENTS

| EP | 2777506 A1 | 9/2014 |
| JP | 08-010257 A | 1/1996 |
| (Continued) | | |

OTHER PUBLICATIONS

Extended European Search Report dated Jun. 27, 2016 issued in European Patent Application No. 16151859.2.

*Primary Examiner* — Pascal M Bui Pho
*Assistant Examiner* — Marjan Saboktakin
(74) *Attorney, Agent, or Firm* — Morgan, Lewis & Bockius LLP

(57) ABSTRACT

Provided is an ultrasound system configured to detect a flow noise signal at a phantom gate and display a visual indictor representing the detected flow noise signal. The ultrasound system transmits ultrasound signals to an object including a sample volume and receives echo signals from the sample volume and at least one phantom gate. The ultrasound system also generates an ultrasound image based on the received echo signals and displays the generated ultrasound image. Furthermore, the ultrasound system detects a flow noise signal at the at least one phantom gate by using the echo signals and displays a visual indicator representing the detected flow noise signal together with the ultrasound image.

24 Claims, 12 Drawing Sheets

(51) Int. Cl.
  *A61B 8/08* (2006.01)
  *A61B 8/06* (2006.01)
  *G01S 7/52* (2006.01)
(52) U.S. Cl.
  CPC ........... *A61B 8/4461* (2013.01); *A61B 8/4472* (2013.01); *A61B 8/565* (2013.01)

(56) References Cited

U.S. PATENT DOCUMENTS

| | | | |
|---|---|---|---|
| 6,364,838 | B1 | 4/2002 | Freiburger et al. |
| 6,663,566 | B2 | 12/2003 | Pan et al. |
| 7,901,358 | B2 | 3/2011 | Mehi et al. |
| 2003/0163043 | A1* | 8/2003 | Heimdal ............. G01S 7/52042 600/437 |
| 2006/0079782 | A1 | 4/2006 | Beach et al. |
| 2009/0326379 | A1 | 12/2009 | Daigle et al. |
| 2010/0004540 | A1 | 1/2010 | Thiele |
| 2010/0234729 | A1 | 9/2010 | Bae et al. |
| 2011/0178406 | A1* | 7/2011 | Shuangshuang .... G01S 7/52019 600/453 |
| 2012/0157848 | A1 | 6/2012 | Kim |
| 2012/0283564 | A1 | 11/2012 | Ebbini et al. |
| 2013/0165785 | A1* | 6/2013 | Lause ...................... A61B 8/06 600/443 |
| 2014/0114189 | A1 | 4/2014 | Kanayama et al. |
| 2014/0276057 | A1* | 9/2014 | Lee ........................ A61B 8/469 600/441 |
| 2015/0320396 | A1* | 11/2015 | Abe ..................... A61B 8/5207 600/443 |

FOREIGN PATENT DOCUMENTS

| | | |
|---|---|---|
| JP | 2009-213566 A | 9/2009 |
| JP | 2013-005876 A | 1/2013 |
| KR | 10-2009-0042152 A | 4/2009 |
| KR | 10-2012-0067535 A | 6/2012 |

* cited by examiner

410

FIG. 5
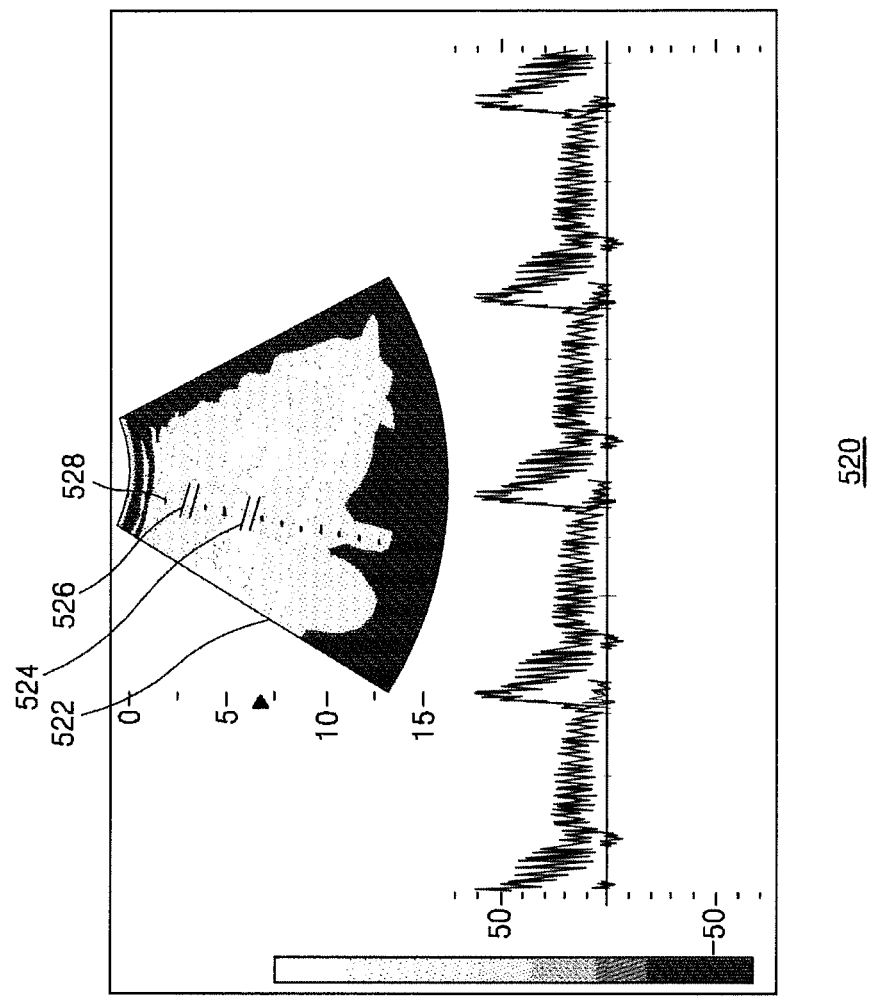
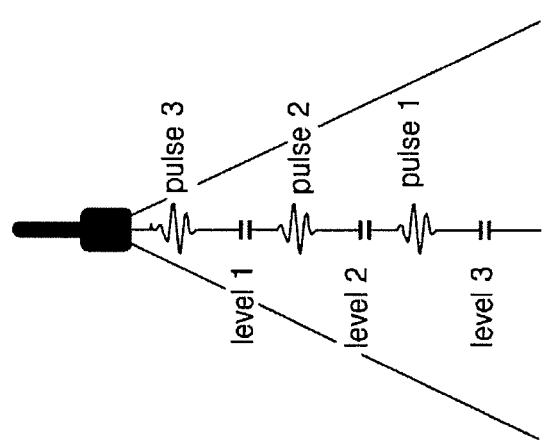

FIG. 7A
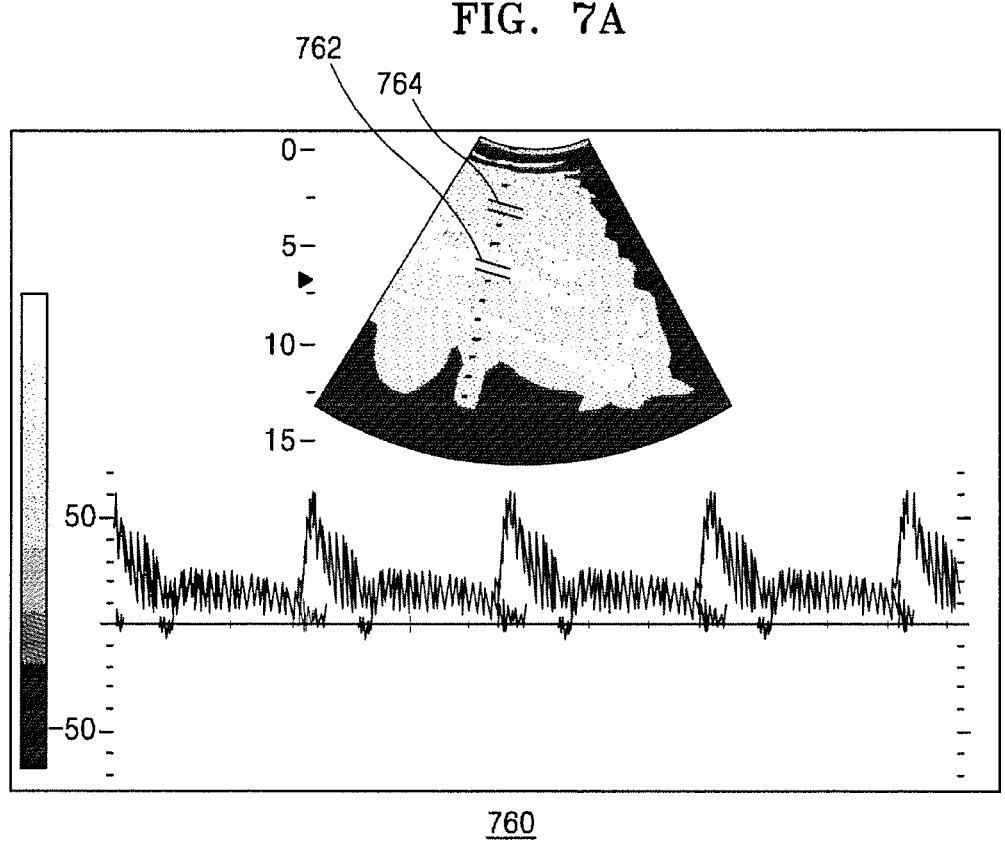
760
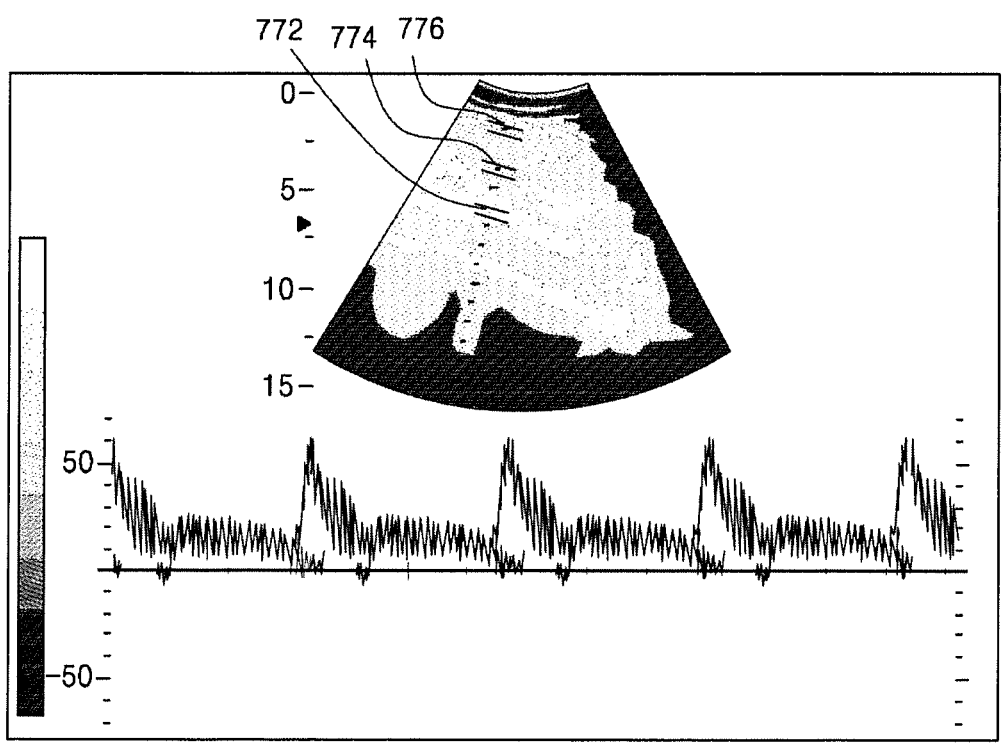
770

ULTRASOUND SYSTEM AND METHOD OF PROVIDING GUIDE FOR IMPROVED HPRF DOPPLER IMAGE

CROSS-REFERENCE TO RELATED APPLICATION

This application claims the benefit of Korean Patent Application No. 10-2015-0015580, filed on Jan. 30, 2015, in the Korean Intellectual Property Office, the disclosure of which is incorporated herein in its entirety by reference.

BACKGROUND

1. Field

The present disclosure relates to ultrasound systems and methods of providing a guide for a high pulse repetition frequency (HPRF) Doppler image, and more particularly, to an ultrasound system and method of providing a visual guide for improving quality of a HPRF Doppler image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

In addition, an ultrasound system provides a Doppler image by using a pulse repetition frequency (PRF) that is higher than a generally available PRF in order to detect blood flow having a velocity higher than a maximum detectable flow velocity from a deep part having a specific depth. The Doppler image is called a HPRF Doppler image. Since a HPRF Doppler image may contain a noise signal due to inherent characteristics, it is necessary to develop a method of improving quality of the HPRF Doppler image.

SUMMARY

Provided are ultrasound systems and methods of providing a visual guide for improving quality of a high pulse repetition frequency (HPRF) Doppler image.

Additional aspects will be set forth in part in the description which follows and, in part, will be apparent from the description, or may be learned by practice of the presented exemplary embodiments.

According to an aspect of an exemplary embodiment, an ultrasound system includes: An ultrasound system comprising: an ultrasound transceiver configured to transmit ultrasound signals to an object including a sample volume and receive echo signals from the sample volume and at least one phantom gate; a processor configured to generate an ultrasound image based on the received echo signals; and a display configured to display the generated ultrasound image, wherein the processor detects a flow noise signal at the at least one phantom gate by using the echo signals and controls the display to display a visual indicator representing the detected flow noise signal.

The processor controls the ultrasound transceiver to repeat, by a predetermined ensemble number, an operation of transmitting the ultrasound signals along a pulsed Doppler line passing through the sample volume and receiving the echo signals from the sample volume and the at least one phantom gate, and wherein the predetermined ensemble number of the received echo signals comprise echo signals reflected from a plurality of positions included in the pulsed Doppler line.

The processor analyzes ultrasound data corresponding to a position of the at least one phantom gate from among ultrasound data generated based on the received echo signals reflected from the plurality of positions and detects the flow noise signal based on a result of the analyzing.

The ultrasound transceiver transmits the ultrasound signals by using an aperture in a maximum aperture and receives some of the echo signals by using another aperture that is different from the aperture in the maximum aperture, and wherein the processor detects the flow noise signal at the phantom gate based on the some echo signals received using the other aperture.

The processor controls, based on a point where the aperture is located relative to the maximum aperture, the other aperture to be located at a point not overlapping the point where the aperture is located.

To detect the flow noise signal, the processor uses at least one algorithm from among Auto-correlation, Cross-correlation, Fast Fourier Transform, and Phase Locked Loop to analyze the echo signals.

The processor controls the display to display the visual indicator only when a magnitude of the detected flow noise signal is greater than or equal to a predetermined threshold value.

The visual indicator comprises a message indicating that the flow noise signal has been detected at the at least one phantom gate.

The processor controls the visual indicator to be displayed at a position of a phantom gate where the flow noise signal has been detected in such a manner that the position of the phantom gate is distinguished from neighboring regions.

The ultrasound system further includes a user interface including a plurality of control items, wherein the processor controls the user interface to display the visual indicator at a position corresponding to at least one control item related to control of the detected flow noise signal from among the plurality of control items.

The display is a touch screen comprising the user interface.

The ultrasound system further includes a user interface, wherein, to avoid the detected flow noise signal, the processor changes, based on a user input via the user interface, a pulse repetition frequency (PRF) of the transmitted ultrasound signals or changes an aperture being used to transmit the ultrasound signals.

To avoid the detected flow noise signal, the processor automatically changes a PRF of the transmitted ultrasound signals or automatically changes an aperture being used to transmit the ultrasound signals.

According to an aspect of another exemplary embodiment, a method of displaying an ultrasound image, the method includes transmitting ultrasound signals to an object including a sample volume and receiving echo signals from the sample volume and at least one phantom gate; generating the ultrasound image based on the received echo signals; and detecting a flow noise signal at the at least one phantom gate by using the echo signals; and displaying a visual indicator representing the detected flow noise signal together with the generated ultrasound image.

The transmitting of the ultrasound signals and the receiving of the echo signals comprises repeating, by a predetermined ensemble number, an operation of transmitting the ultrasound signals along a pulsed Doppler line passing through the sample volume and receiving the echo signals from the sample volume and the at least one phantom gate, and wherein the predetermined ensemble number of the received echo signals comprise echo signals reflected from a plurality of positions included in the pulsed Doppler line.

The detecting of the flow noise signal comprises analyzing ultrasound data corresponding to a position of the at least one phantom gate from among ultrasound data generated based on the received echo signals reflected from the plurality of positions and detecting the flow noise signal based on a result of the analyzing.

The ultrasound signals are transmitted by using an aperture in a maximum aperture, and some of the echo signals are received by using another aperture that is different from the aperture in the maximum aperture, and wherein the flow noise signal is detected at the phantom gate based on the some echo signals received using the other aperture.

A point where the other aperture is located is determined based on a point where the aperture is located relative to the maximum aperture.

The flow noise signal is detected by analyzing the echo signals by using at least one algorithm from among Autocorrelation, Cross-correlation, Fast Fourier Transform, and Phase Locked Loop.

The visual indicator is displayed only when a magnitude of the detected flow noise signal is greater than or equal to a predetermined threshold value.

The visual indicator comprises a message indicating that the flow noise signal has been detected at the at least one phantom gate.

The visual indicator is displayed at a position of a phantom gate where the flow noise signal has been detected so that the position of the phantom gate is distinguished from neighboring regions.

The visual indicator is displayed at a position corresponding to at least one control item related to control of the detected flow noise signal in a user interface comprising a plurality of control items.

The method may further include, to avoid the detected flow noise signal, changing a pulse repetition frequency (PRF) of the transmitted ultrasound signals or an aperture being used to transmit the ultrasound signals based on a user input via a user interface.

The method may further include, to avoid the detected flow noise signal, automatically changing a PRF of the transmitted ultrasound signals or automatically changing an aperture being used to transmit the ultrasound signals.

A non-transitory computer-readable recording medium having recorded thereon a program for executing the method.

According to an aspect of another exemplary embodiment, an ultrasound system includes an ultrasound transceiver configured to transmit ultrasound signals to an object including a sample volume and receive echo signals from the sample volume and at least one phantom gate; a processor configured to generate an ultrasound image based on the received echo signals; and a display configured to display the generated ultrasound image, wherein, when a flow noise signal is detected at the at least one phantom gate by using the echo signals, the processor automatically changes a parameter related to transmission of the ultrasound signals so that a phantom gate is generated at a position other than a position of the at least one phantom gate.

The parameter comprises at least one of information about a pulse repetition frequency (PRF) at which the ultrasound signals are transmitted and information about a position of an aperture being used to transmit the ultrasound signals, and wherein, in order to avoid the flow noise signal, the processor performs at least one of an operation of automatically changing the PRF and an operation of automatically controlling the ultrasound transceiver to transmit the ultrasound signals by using another aperture located at a position different from the position of the aperture.

BRIEF DESCRIPTION OF THE DRAWINGS

Embodiments of the inventive concept now will be described more fully hereinafter with reference to the accompanying drawings, in which reference numerals denote structural elements:

FIG. 5 is a diagram related to an ultrasound system for acquiring a Doppler image by transmitting a pulse wave having a high pulse repetition frequency (HPRF) that is higher than a general PRF, according to an exemplary embodiment;

FIGS. 7A through 7C illustrate visual indicators displayed when a flow noise signal is detected at a phantom gate, according to exemplary embodiments;

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments will be described in detail with reference to the accompanying drawings.

Figure 1:
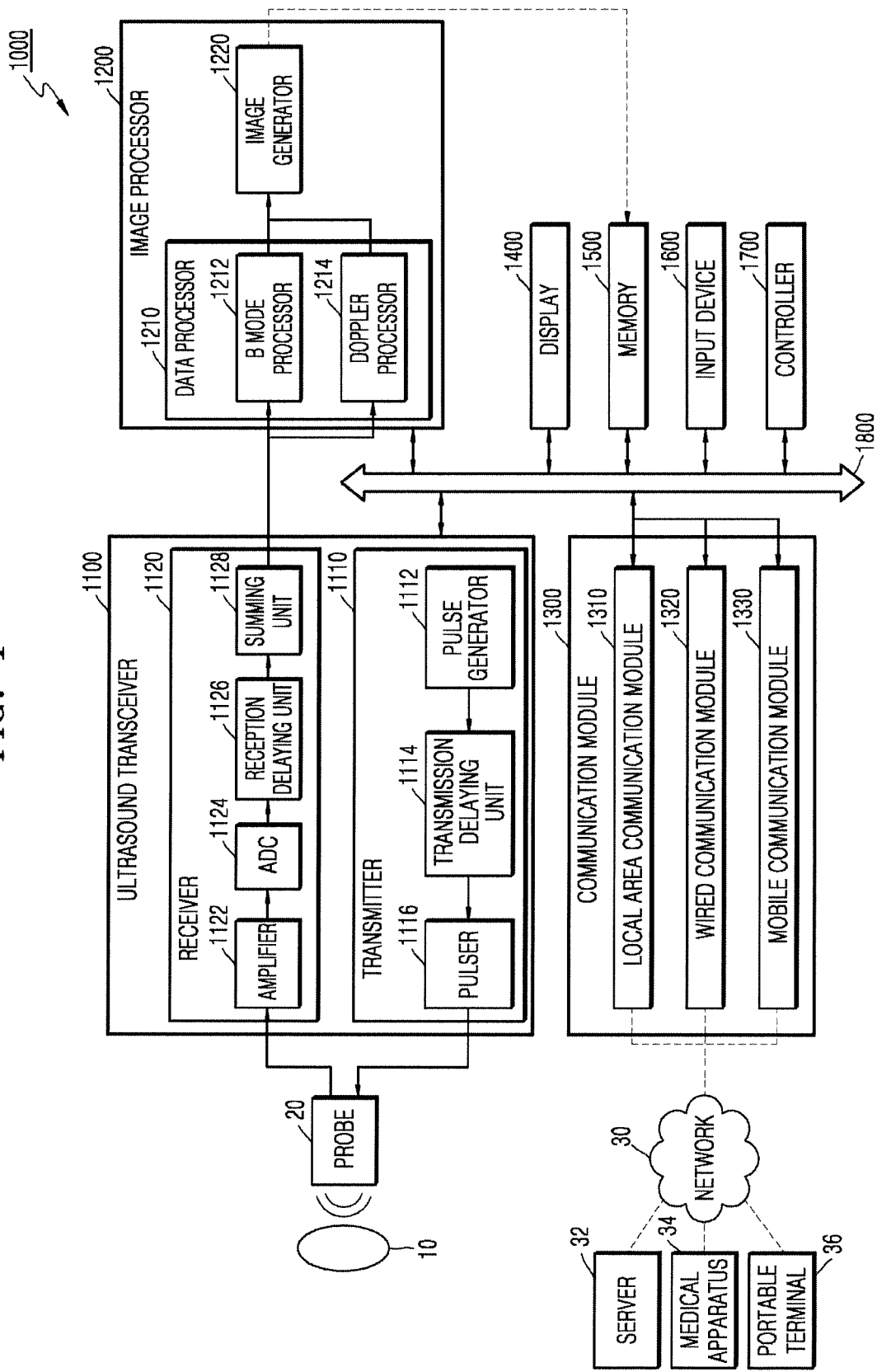
FIG. 1 is a block diagram showing a configuration of an ultrasound diagnosis apparatus according to an exemplary embodiment.

FIG. 1 is a block diagram showing a configuration of an ultrasound diagnosis apparatus 1000 according to an embodiment. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Also, at least one of the ultrasound transmission/reception unit 1100, the image processor 1200, and the communication module 1300 may be included in the control unit 1600; however, the inventive concept is not limited thereto.

Figure 2:
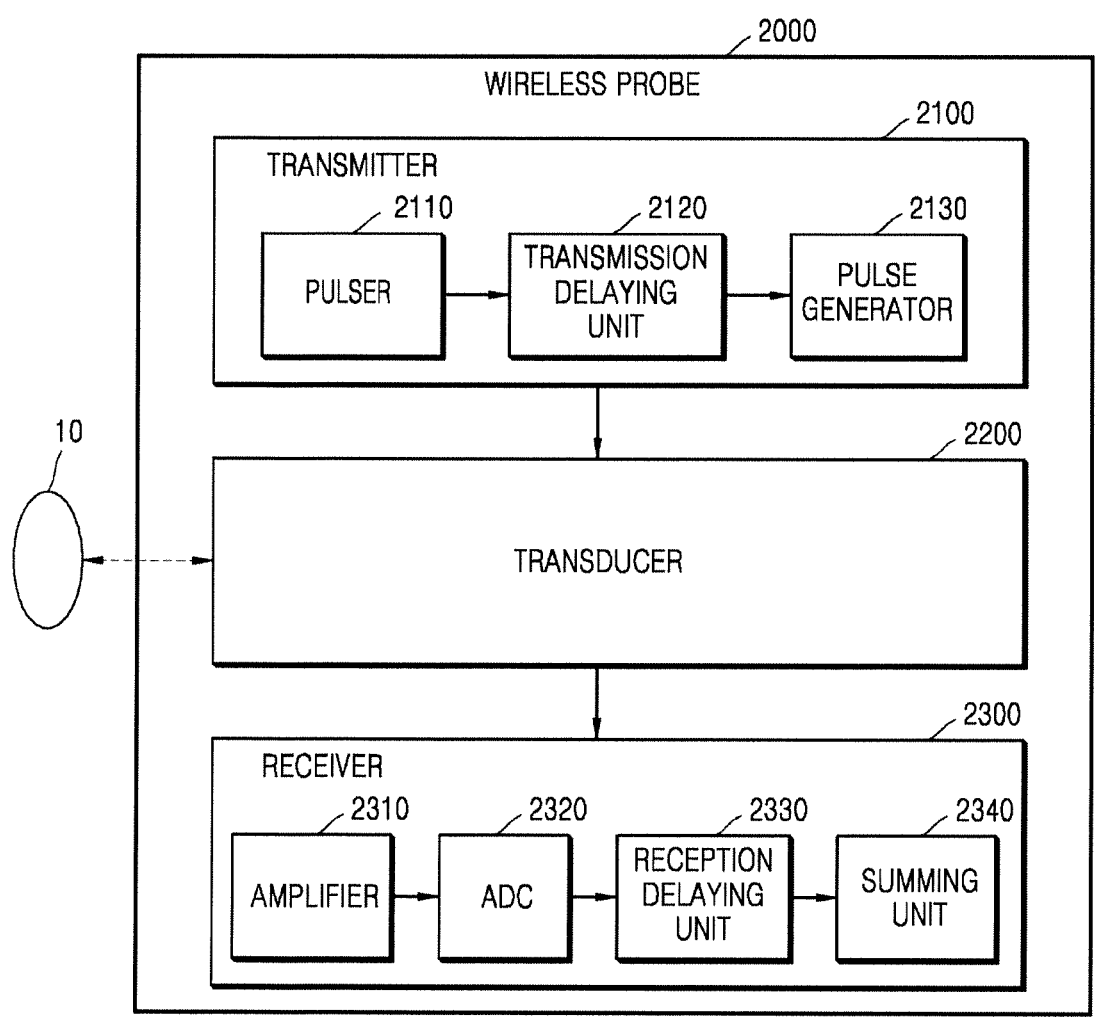
FIG. 2 is a block diagram showing a configuration of a wireless probe according to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

Figure 3:
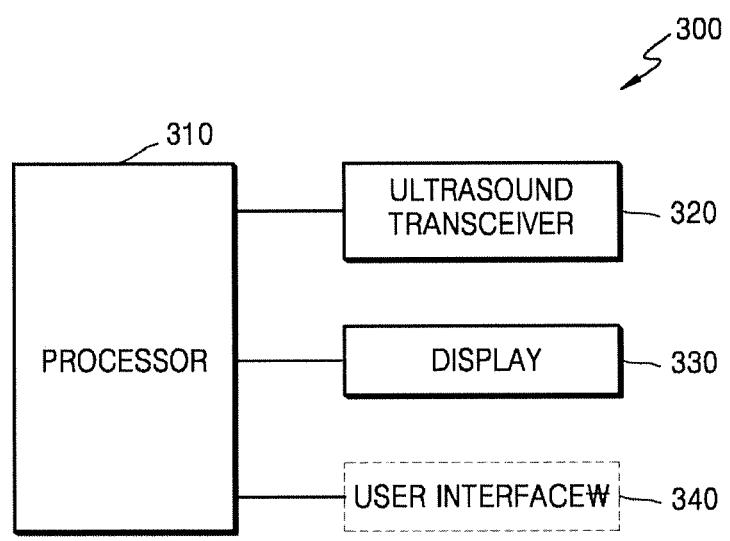
FIG. 3 is a schematic diagram of a configuration of an ultrasound system according to an exemplary embodiment.

FIG. 3 is a schematic diagram of a configuration of an ultrasound system 300 according to an exemplary embodiment. The ultrasound system 300 according to the present exemplary embodiment may be included in the ultrasound diagnosis apparatus 1000 and a method of displaying an ultrasound image via the ultrasound system 300 may be performed by the ultrasound diagnosis apparatus 1000 of FIG. 1.

According to an exemplary embodiment, the ultrasound system 300 includes a processor 310, an ultrasound transceiver 320, and a display 330. The ultrasound system 300 may perform all or some of the functions of the ultrasound diagnosis apparatus 1000. For example, the ultrasound transceiver 320 and the display 330 of the ultrasound system 300 may respectively correspond to the ultrasound transceiver 1100 and the display 1400 described with reference to FIG. 1. The processor 310 may include some of the components and functions of the image processor 1200 and the controller 1700 described with reference to FIG. 1. According to an exemplary embodiment, the processor 310 may be separated into a plurality of processors to perform the functions of the image processor 1200 and the controller 1700, or a single processor may perform all of the functions of the image processor 1200 and the controller 1700.

The ultrasound transceiver 320 transmits ultrasound signals to an object including a sample volume and receives echo signals reflected by the object. In this case, the ultrasound transceiver 320 may transmit an ultrasound signal as a pulse wave intersecting the sample volume along a pulsed Doppler line and receive an echo signal reflected from the sample volume or at least one phantom gate. A phantom gate may also be referred to as a virtual sample volume. Furthermore, the ultrasound transceiver 320 may receive echo signals not only from the sample volume or the at least one phantom gate but also from each of points (positions) in the pulsed Doppler line, other than the sample volume or the at least one phantom gate.

The processor 310 may generate an ultrasound image based on received echo signals. Furthermore, the processor 310 may detect a flow noise signal at at least one phantom gate by using the received echo signals and control the display 330 to display a visual indicator representing the detected flow noise signal.

Figure 4A:
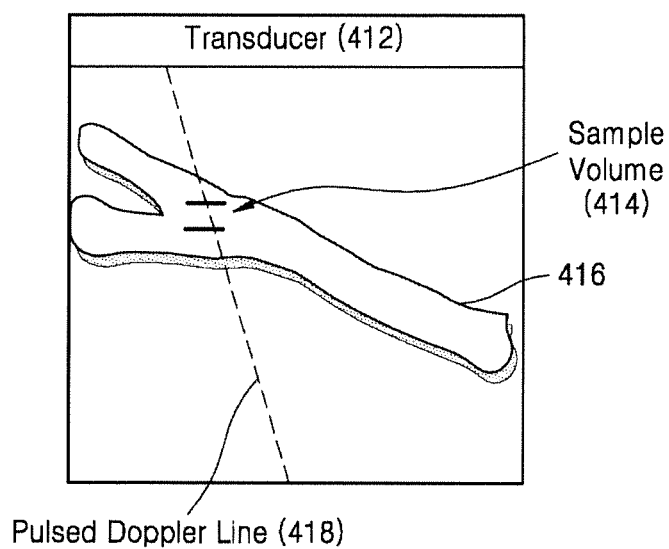
FIGS. 4A and 4B schematically illustrate ultrasound images generated by an ultrasound system according to an exemplary embodiment.

In a method of detecting a flow noise signal at a phantom gate, according to an exemplary embodiment, referring to FIG. 4A, an ultrasound image 410 shows a cross-section of an object including a moving object such as a blood vessel 416. In order to measure blood flow velocity at the sample volume 414 located in the blood vessel 416, the ultrasound transceiver 320 transmits an ultrasound pulse wave along a pulsed Doppler line 318 passing through a position of the sample volume 414. In this case, the ultrasound pulse wave may be transmitted at a PRF. An ultrasound probe including a plurality of transducers 412 is located over the cross-section of the object depicted in the ultrasound image 410.

In addition, to detect a flow noise signal at a phantom gate, the processor 310 may control the ultrasound transceiver 320 to repeat an operation of transmitting an ultrasound signal along the pulsed Doppler line 318 passing through the sample volume 414 and receiving an echo signal from the sample volume 414 by a predetermined ensemble number. An ensemble number may also be referred to as an ensemble length or ensemble size. In this case, the ultrasound signal that is repeatedly transmitted by the predetermined ensemble number may be the same as or different from an ultrasound signal that is transmitted at a PRF to measure blood flow velocity at the sample volume 414. According to an exemplary embodiment, the ultrasound transceiver 320 may alternately perform an operation of transmitting and receiving ultrasound signals at a PRF to measure blood flow velocity at the sample volume 414 and an operation of transmitting and receiving ultrasound signals by an ensemble number to measure Doppler information at points other than the sample volume 414 on the pulsed Doppler line 318.

The processor 310 may acquire Doppler information at a plurality of points (or positions) or at all respective points (or positions) included in the pulsed Doppler line 318 based on a predetermined ensemble number of received echo signals. In general, a pulsed wave (PW) Doppler system performs a range gate operation, i.e., a sample & hold operation on an output of an ultrasound signal, based on information about a position of a specific sample volume at which Doppler information is to be acquired and a PRF. However, the ultrasound system 300 according to the exemplary embodiment is configured to receive an ensemble number of echo signals by repeatedly transmitting ultrasound signals by the ensemble number and acquire Doppler information at a plurality of points (or positions) or at all the respective points (or positions) on the pulsed Doppler line 318 based on the ensemble number of received echo signals.

In addition, the processor 310 determines a position of at least one phantom gate based on a position of the sample volume 414 and a PRF of a pulse wave being transmitted. Then, the processor 310 may produce ultrasound data from an ensemble number of echo signals and acquire Doppler information at the at least one phantom gate by using ultrasound data at a position (point or pixel) in the produced ultrasound data corresponding to the at least one phantom gate.

Figure 4B:
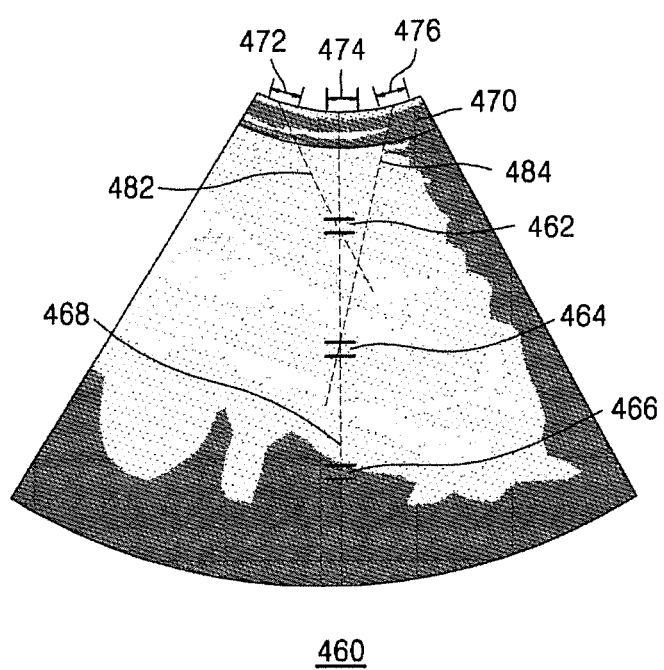

In a method of detecting a flow noise signal at a phantom gate according to another exemplary embodiment, referring to FIG. 4B, an ultrasound image 460 shows a cross-section of an object including a sample volume 466. In order to measure blood flow velocity at the sample volume 466, the ultrasound transceiver 320 transmits an ultrasound pulse wave along a pulsed Doppler line 468 passing through a position of the sample volume 468. In this case, the ultrasound pulse wave may be transmitted via transducers 470 and may have a PRF. In addition, the processor 310 may determine positions of phantom gates formed on the pulsed Doppler line 468 based on the sample volume 466 and the PRF. In this case, it is assumed that first and second phantom gates 462 and 464 are formed.

The ultrasound transceiver 320 may transmit an ultrasound pulse signal along the pulsed Doppler line 468 by using only an aperture 474 for detecting the sample volume 466 in a maximum aperture formed by all the transducers 470. In the present specification, the aperture 474 used to detect the sample volume 466 is hereinafter referred to as a primary aperture 474.

According to an exemplary embodiment, the ultrasound transceiver 320 may use a first adjacent aperture 472 and/or a second adjacent aperture 476 other than the primary aperture 474 to respectively detect flow noise signals at the first and second phantom gates 462 and 464. In this case, the first adjacent aperture 472 and/or the second adjacent aperture 476 may be located at regions in the maximum aperture, which are regions other than that of the primary aperture 474 that is used for transmitting ultrasound waves to detect Doppler information at the sample volume 466. While FIG. 4B shows that the first and second adjacent apertures 472 and 476 are respectively located on left and right sides of the primary aperture 474, they may be located anywhere in the maximum aperture other than the primary aperture 474.

According to an exemplary embodiment, the ultrasound transceiver 320 may receive at least some of echo signals reflected from the first phantom gate 462 by using the first adjacent aperture 472 and receive at least some of echo signals reflected from the second phantom gate 464 by using the second adjacent aperture 476. In this case, the received echo signals may be echo signals reflected and returning from the first phantom gate 462 and/or the second phantom gate 464 after transmitting an ultrasound pulse through the primary aperture 474. According to an exemplary embodiment, when the primary aperture 474 is located to the right of the maximum aperture the ultrasound transceiver 320 may detect a flow noise signal at the first or second phantom gate 462 or 464 by using the first adjacent aperture 472 located to the left of the maximum aperture. On the other hand, when the primary aperture 474 is located to the left of the maximum aperture, the ultrasound transceiver 320 may detect a flow noise signal at the first or second phantom gate 462 or 464 by using the second adjacent aperture 476 located to the right of the maximum aperture.

To select an echo signal reflected from the first phantom gate 462 from among echo signals reflected and returning from an object after transmitting a ultrasound pulse wave through the primary aperture 474 and receive the selected echo signal, the first adjacent aperture 472 may perform a range gate operation based on information about a PRF of a transmitted ultrasound pulse signal and information about a distance from the first adjacent aperture 472 to the first phantom gate 462. The second adjacent aperture 476 may also operate in a similar way to select an echo signal reflected from the second phantom gate 464 from among echo signals reflected from and returning from the object after transmitting a ultrasound pulse wave through the primary aperture 474 and receive the selected echo signal.

The processor 310 may detect a flow noise signal at a first phantom gate 462 and/or a second phantom gate 464, based on an echo signal received at the first adjacent aperture 472 and/or an echo signal received at the second adjacent aperture 476.

When flow noise signals are to be detected at the first and second phantom gates 462 and 464 by using the primary aperture 474, the ultrasound transceiver 320 needs to suspend transmission and reception of an ultrasound signal so as to acquire Doppler information at the sample volume 466 and to perform transmission and reception of an ultrasound signal so as to detect flow noise signals at the first and second phantom gates 462 and 464. However, when flow noise signals are detected at the first and second phantom gates 462 and 464 by using the first and second adjacent apertures 472 and 476, the ultrasound transceiver 320 does not need to suspend transmission and reception of an ultrasound signal in order to acquire Doppler information at the sample volume 466. In other words, the ultrasound system 300 may detect flow noise signals at the first and second phantom gates 462 and 464 while simultaneously or in real-time performing without interruption a Doppler imaging mode in which Doppler information is acquired at the sample volume 466 and displayed.

Referring back to FIG. 3, the display 330 may display a visual indicator representing a flow noise signal detected at at least one phantom gate according to control by the processor 310.

Furthermore, according to an exemplary embodiment, the ultrasound system 300 may further include a user interface 340. However, the user interface 340 is not an essential component. The user interface 340 may receive from a user an input for controlling processing and displaying of an ultrasound image. In particular, the user interface 340 may receive a user input for controlling a function related to reduction of a detected flow noise signal.

A configuration and functions of the ultrasound system 300 will be described in more detail below.

FIG. 5 is a diagram related to an ultrasound system for acquiring a Doppler image by transmitting a pulse wave having a high PRF (HPRF) higher than a general PRF, according to an exemplary embodiment Although the maximum detectable Doppler flow velocity is determined by a PRF and a central frequency of a pulse wave ultrasound signal, increasing a PRF in order to measure a higher velocity blood flow shortens the time before the next transmission. Thus, the pulse wave ultrasound signal may be transmitted and returned to only a shallow depth before the next transmission, so that a reflected echo signal from a deep depth may not return before the next transmission.

However, even when an initially transmitted ultrasound wave returns from a relatively deep depth and is not received before second transmission, the initially transmitted ultrasound wave will not disappear by itself. As an echo signal is received at a nearby position after a secondarily transmitted ultrasound signal, signals that have not yet arrived after the initially transmitted signal are simultaneously received while being mixed together with the echo signal. Thus, according to an exemplary embodiment, a HPRF pulse wave ultrasound system may acquire Doppler information at a sample volume that is located at a deep depth by using characteristics of a HPRF pulse wave ultrasound signal.

Referring to a conceptual diagram 510 for ultrasound transmission and reception, when a sample volume is located at level 2, the ultrasound transceiver 320 transmits pulse 3 before arrival of an echo signal corresponding to pulse 2. By repeating such a transmission method, the ultrasound transceiver 320 may continuously receive a superposed echo signal in which echo signals respectively from level 1 and level 2 are superposed on each other. When the sample volume is located at level 2, and a phantom gate is located at level 1, the received superposed echo signal may include both Doppler information obtained from the phantom gate located at level 1 and Doppler information obtained from the sample volume located at level 2.

When Doppler information to be acquired by the ultrasound system 300 is Doppler information obtained from the sample volume located at level 2, if motion of an object, i.e., blood flow, occurs in the phantom gate, Doppler information at level 1 may be a noise signal with respect to Doppler information obtained from the sample volume.

According to an exemplary embodiment, an ultrasound image 520 includes a B mode ultrasound image 522 having a pulsed Doppler line 528 shown therein. Furthermore, a sample volume indicator 524 representing a sample volume and a sample gate indicator 526 representing a location of a phantom gate are indicated on the pulsed Doppler line 528. Furthermore, according to an exemplary embodiment, the ultrasound system 300 analyzes a superposed echo signal obtained by superposition of echo signals received from the sample volume and the phantom gate to thereby determine whether a flow noise signal is detected at the phantom gate. When the flow noise signal is detected at the phantom gate, the ultrasound system 300 displays to a user a visual indicator indicating that the flow noise signal has been detected. Detection of a flow noise signal at a phantom gate and displaying of a visual indicator representing the detected flow noise signal will be described in more detail below.

Figure 6:
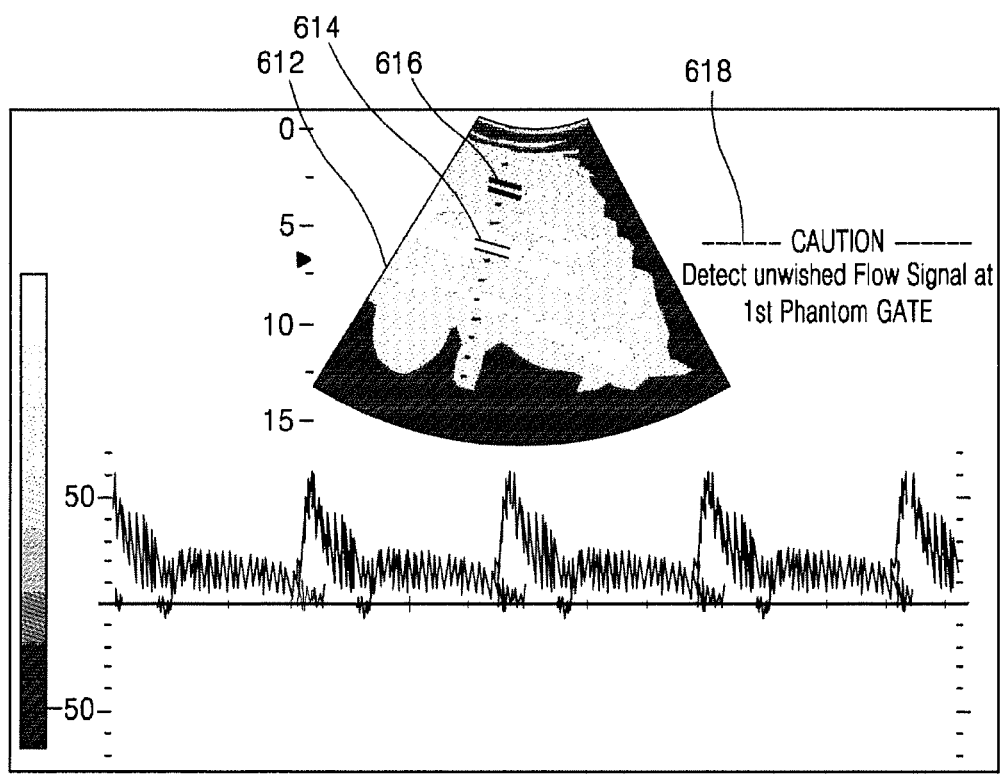
FIG. 6 illustrates an ultrasound image including a HPRF Doppler image generated based on a HPRF ultrasound signal and a visual guide for improving quality of the HPRF Doppler image, according to an exemplary embodiment.

FIG. 6 illustrates an ultrasound image 610 including a HPRF Doppler image generated based on a HPRF ultrasound signal and a visual guide for improving quality of the HPRF Doppler image, according to an exemplary embodiment.

According to an exemplary embodiment, the ultrasound system 300 displays an ultrasound image 610 including a B mode image 612, a sample volume indicator 614 representing a sample volume, and a phantom gate indicator 616 representing a phantom gate, like the ultrasound image 520 shown in FIG. 5. Although the ultrasound image 610 shows the presence of one phantom gate, a plurality of phantom gates may be present in the ultrasound image 610.

The ultrasound system 300 analyzes a superposed echo signal obtained by superposition of echo signals received from the sample volume and the phantom gate to thereby determine whether a flow noise signal is detected at the phantom gate. When the ultrasound system 300 determines that the flow noise signal is detected at the phantom gate, the ultrasound system 300 displays a visual indicator showing a user that the flow noise signal has been detected.

According to an exemplary embodiment, the visual indicator may be a message 618 indicating that a flow noise signal has been detected at a phantom gate According to another exemplary embodiment, the ultrasound system 300 may display the visual indicator by showing a phantom gate indicator representing a phantom gate from which a flow noise signal is detected in a different color, thickness, or shape than its neighboring regions. According to another exemplary embodiment, the ultrasound system 300 may display the visual indicator by showing a phantom gate indicator representing a phantom gate from which a flow noise signal is detected in such a manner as to flash on and off.

Figure 7B:
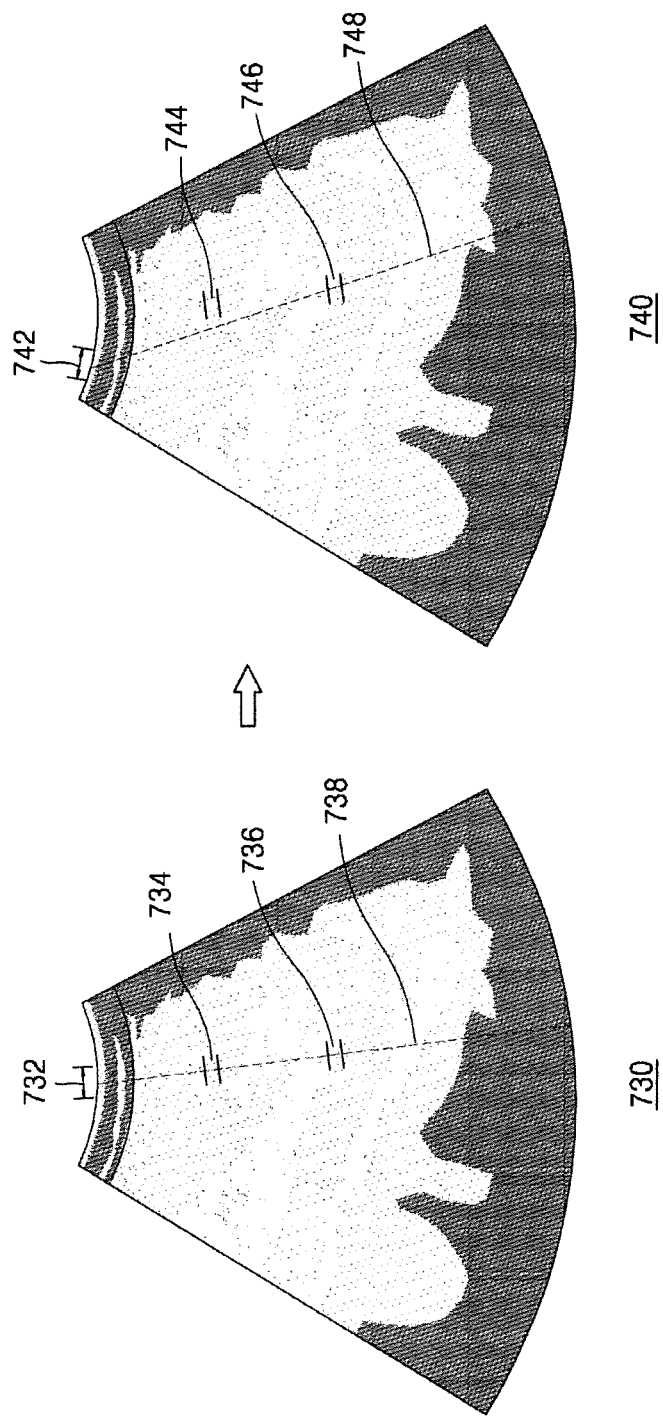
Figure 7C:
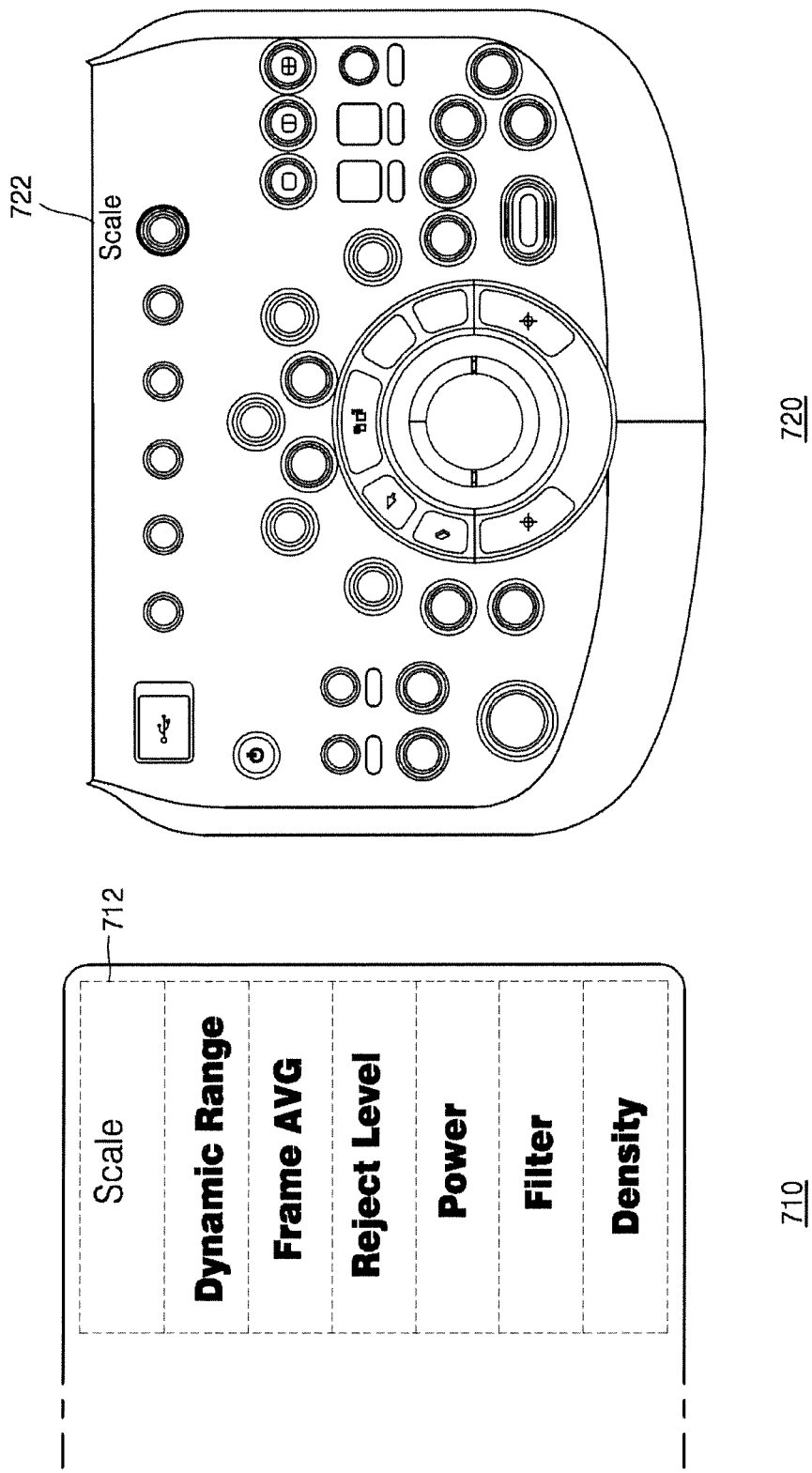

FIGS. 7A through 7C illustrate operations performed by the ultrasound system 300 when a flow noise signal is detected at a phantom gate, according to exemplary embodiments.

Referring to FIG. 7A, in an ultrasound image 760 according to an exemplary embodiment, to acquire Doppler information at a sample volume 762, a phantom gate 764 is generated for an ultrasound signal transmitted at a first PRF. In this case, if a flow noise signal is detected at the phantom gate 764, the user may control a phantom gate to occur at a different location by increasing or decreasing a PRF via the user interface 340. In this way, to acquire Doppler information at a sample volume 772 (that is at the same location as the sample volume 762), phantom gates 774 and 776 are generated for an ultrasound signal transmitted at a second PRF. Accordingly, a phantom gate is not generated at a location corresponding to the phantom gate 764 generated for the ultrasound signal transmitted at the first PRF. Thus, the user may acquire Doppler information at the sample volume 772 without having a flow noise signal that was detected at the phantom gate 764.

Furthermore, if a flow noise signal is detected at the phantom gate 764, the ultrasound system 300 may control a phantom gate to occur at a different location by automatically increasing or decreasing a PRF without receiving a separate input from the user. In this case, the ultrasound system 300 adjusts a PRF so that a phantom gate is generated at a location different than a location corresponding to the phantom gate 764. According to an exemplary embodiment, when it is determined that there are a plurality of PRFs that may be adjusted so that phantom gates are generated at locations different than the location corresponding to the phantom gate 764, the ultrasound system 300 may automatically select, from among the plurality of PRFs, a PRF at which a flow noise signal having a smallest magnitude is detected at one of the phantom gates generated at different locations and acquire Doppler information at the sample volume 772 by using the selected PRF. According to another exemplary embodiment, the ultrasound system 300 may select one of a plurality PRFs at which a magnitude of a flow noise signal detected at one of a phantom gates generated at different locations according to adjusted PRFs is less than or equal to a predetermined threshold value and acquire Doppler information at the sample volume 772 by using the selected PRF.

Furthermore, referring to FIG. 7B, an ultrasound image 730 according to an exemplary embodiment shows transmission of an ultrasound signal through a first aperture 732 along a first pulsed Doppler line 738 in order to acquire Doppler information at a sample volume 736. The ultrasound system 300 detects a flow noise signal at a phantom gate 734. In this case, the user changes, via the user interface 340, an aperture to be used to acquire Doppler information at the sample volume 736. A PRF at which the ultrasound signal is transmitted may be changed based on a user input when needed. An ultrasound image 740 shows transmission of an ultrasound signal through a new second aperture 742 along a second pulsed Doppler line 748 based on a user input. In this case, the second pulsed Doppler line 748 passes through a sample volume 746 that is at the same location as the sample volume 736. Thus, due to the use of the second pulsed Doppler line 748 not passing through the phantom gate 734 at which a flow noise signal has been detected, the ultrasound system 300 may acquire Doppler information at the same volume 746 without having a flow noise signal at a location 744 corresponding to the phantom gate 734.

Furthermore, according to an exemplary embodiment, if a flow noise signal is detected at the phantom gate 734, the ultrasound system 300 may automatically change positions of an aperture and a pulsed Doppler line to be used without receiving a separate input from the user. Furthermore, when needed, the ultrasound system 300 may automatically change a PRF. The ultrasound system 300 may determine the second aperture 742 and the second pulsed Doppler line 748 to be used by taking into account various factors such as conditions in which a magnitude of a flow noise signal detected at a new phantom gate is the smallest or less than or equal to a predetermined threshold value.

Accordingly, if a flow noise signal is detected at the phantom gate 734 during acquisition of Doppler information at the sample volume 736, the ultrasound system 300 may acquire Doppler information at the sample volume 736 by automatically avoiding a flow noise signal without separate manipulation by the user.

In addition, referring to FIG. 7C, according to an exemplary embodiment, the ultrasound system 300 may include the user interface (340 of FIG. 3) for receiving an input related to a function of adjusting an ultrasound image from the user. For example, the user interface 340 may include a touch panel 710 configured to receive a touch input. The touch panel 710 may be included in the display 330 of the ultrasound system 300 or be implemented as an input unit having a separate touch function. Alternatively, the user interface 340 may include a control panel 720 including buttons implemented using hardware or software.

According to an exemplary embodiment, if a flow noise signal is detected at a phantom gate, the ultrasound system 300 may control control items used for controlling the flow noise signal from among a plurality of control items included in the user interface 340 to be displayed in such a manner as to be distinguished from the other control items.

According to an exemplary embodiment, the user interface 340 includes the touch panel 710, and the touch panel 710 includes a plurality of control items Scale, Dynamic Range, Frame AVG, Reject Level, Power, Filter, and Density. In particular, the plurality of controls items may include the control item "Scale" 712 for performing a function of increasing or decreasing a PRF. As the PRF is increased or decreased, a location where a phantom gate is generated may vary. Thus, a phantom gate is newly generated at a location where a flow noise signal is not detected and not at a location where the flow noise signal has been detected. According to another exemplary embodiment, the plurality of control items may include control items for changing positions of an aperture and a pulsed Doppler line used for acquiring Doppler information at a sample volume.

If a flow noise signal is detected at a phantom gate, the processor 310 may control the control item "Scale" 712 on the touch panel 710 or control items for changing the positions of an aperture and a pulsed Doppler line to be displayed in such a manner as to be distinguished from the other control items thereon, thereby inducing the user to perform user manipulation for reducing the flow noise signal. For example, the processor 310 may control the touch panel 710 to display the control item "Scale" 712 in a different size or color than the other control items or by flashing on and off.

As another example, when the user interface 340 includes the control panel 720, the control panel 720 may include a "Scale" button 722 for performing a function of increasing or decreasing a PRF from among a plurality of buttons. If a flow noise signal is detected at a phantom gate, the processor 310 may control the "Scale" button 722 on the control panel 720 to be displayed in such a manner as to be distinguished from or emphasized more than the other buttons thereon. For example, the processor 310 may control the "Scale" button 722 to be displayed in a manner that allows a color of the "Scale" button 722 or its background to change or the displayed color to flash on and off.

In addition, when PRF is increased or decreased in order to acquire Doppler information at a specific sample volume, at least one of the number of generated phantom gates and a location of a phantom gate may vary. Thus, if a flow noise signal is detected at a specific phantom gate, adjusting a PRF may allow a phantom gate to be generated at a location different than a location where the flow noise signal was detected.

Figure 8:
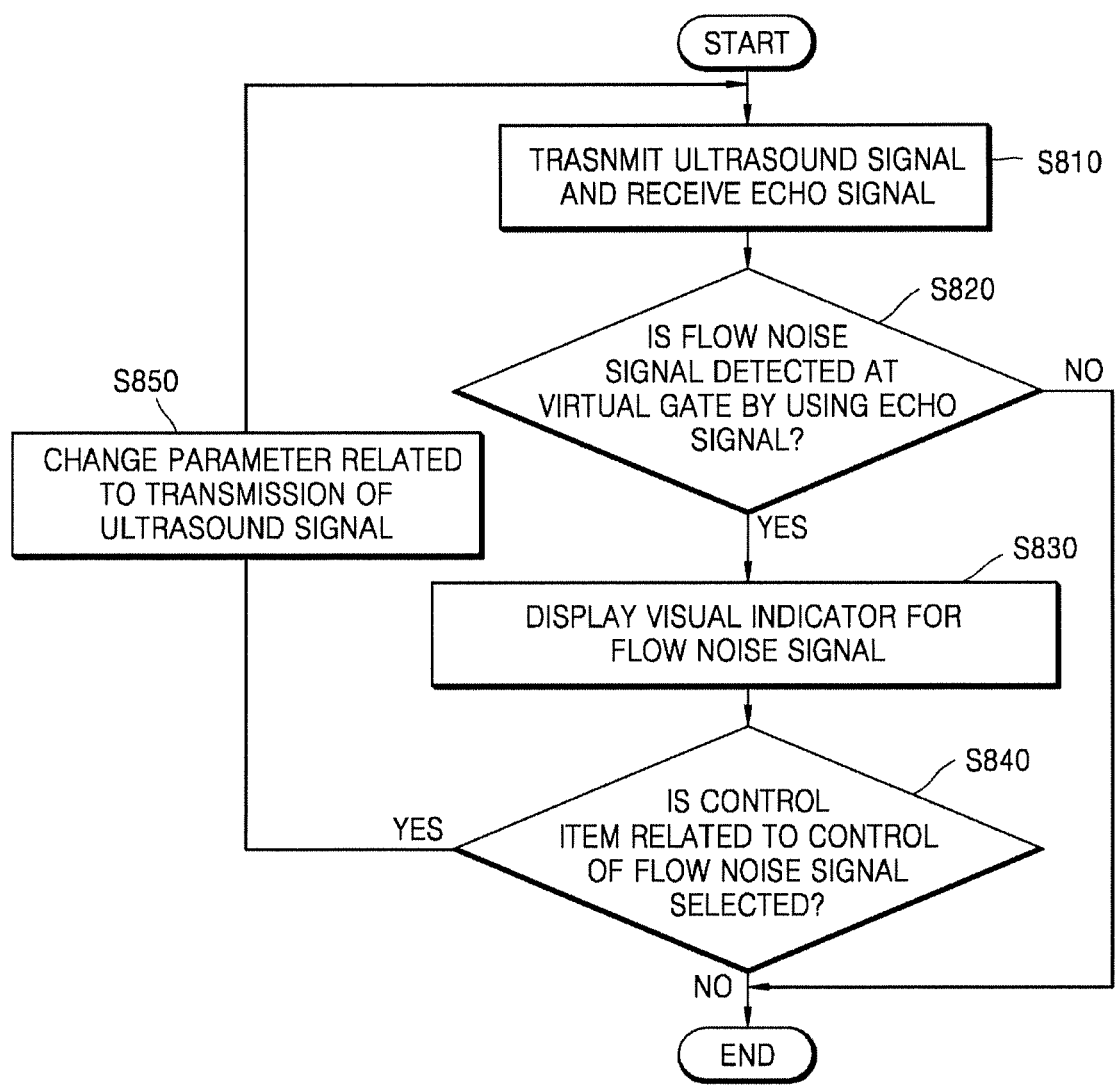
FIG. 8 is a flowchart of a method of providing a guide for a HPRF Doppler image, according to an exemplary embodiment.

FIG. 8 is a flowchart of a method of providing a guide for a HPRF Doppler image according to an exemplary embodiment.

The ultrasound system 300 transmits an ultrasound signal having a first PRF to an object including a sample volume and receives an echo signal from the sample volume and at least one phantom gate (S810). In the received echo signal, an echo signal from the sample volume and an echo signal from the at least one phantom gate are superposed on each other.

By detecting a flow noise signal at a phantom gate from the received echo signal according to a predetermined algorithm, the ultrasound system 300 determines whether the flow noise signal is present in the phantom gate (S820).

When the ultrasound system 300 determines that the flow noise signal is not present in the phantom gate in operation S820, the ultrasound system 300 terminates a method of providing a guide for a HPRF Doppler image. Terminating the method of providing a guide for a HPRF Doppler image means that the ultrasound system 300 displays an ultrasound image of the object but does not display a visual indicator indicating that the flow noise signal has been detected at the phantom gate. According to an exemplary embodiment. When the flow noise signal is not detected at the phantom gate, i.e., when the ultrasound system 300 determines that the flow noise signal is not present in the phantom gate, the ultrasound system 300 may display a visual indicator indicating that the flow noise signal has not been detected at the phantom gate, together with an ultrasound image of the object. In this case, the visual indicator may include a message indicating that the flow noise signal has not been detected.

When the ultrasound system 300 determines that the flow noise signal is present in the phantom gate in operation S820, the ultrasound system 300 performs operation S830. The ultrasound system 300 displays a visual indicator indicating that the flow noise signal has been detected at the phantom gate (S830). The visual indicator nay be displayed on the display 330 according to control by the processor 310.

According to an exemplary embodiment, the visual indicator may be a message indicating that the flow noise signal has been detected at the phantom gate. According to another exemplary embodiment, the processor 310 may control the visual indicator to be displayed at a location of the phantom gate where the flow noise signal has been detected in a different color or size or in such a manner as to flash on and off, so that the user may distinctly recognize the location of the phantom According to an exemplary embodiment, the ultrasound system 300 may further include an audio output unit (e. g., a speaker), and the processor 310 may control the audio output unit to output an audio indicator indicating that a flow noise signal has been detected at a phantom gate. The audio indicator may include audio representing a location or order of the phantom gate where the flow noise signal has been detected from among a plurality of phantom gates.

According to another exemplary embodiment, the ultrasound system 300 may include the user interface 340 including a plurality of control items. In operation S830, the processor 310 may control control items having a function of controlling a flow noise signal from among the plurality of control items included in the user interface 340 to be displayed in such a manner as to be distinguished from the other control items, as described above with reference to FIG. 8A.

The ultrasound system 300 determines whether a user input for selecting a control item related to control of a flow noise signal via the user interface 340 has been received (S840). When the ultrasound system 300 determines that a user input for selecting a control item related to control of a flow noise signal has not been received, the ultrasound system 300 terminates a method of providing a guide for a HPRF Doppler image. In this case, when the ultrasound system 300 terminates the method of providing a guide for a HPRF Doppler image, the ultrasound system 300 maintains a state in which the visual indicator, which indicates that a flow noise signal has been detected at a phantom gate, is displayed while displaying an ultrasound image of the object. According to an exemplary embodiment, after a lapse of a predetermined time from a time point at which the visual indicator is displayed, the processor 310 may control the visual indicator not to be displayed any more or to be displayed intermittently.

When the ultrasound system 300 determines that a user input for selecting a control item related to control of a flow noise signal is received, the ultrasound system 300 performs operation S850. According to an exemplary embodiment, the user input for selecting a control item related to control of a flow noise signal may be an input for selecting a control item related to a function of increasing or decreasing a PRF of an ultrasound signal being transmitted or a control item related to a function of changing positions of an aperture and a pulsed Doppler line being used for acquiring Doppler information at a sample volume.

The ultrasound system 300 changes a parameter related to transmission of an ultrasound signal based on the user input whose reception is determined in operation S840 (S850). According to an exemplary embodiment, the ultrasound system 300 may increase or decrease a PRF of an ultrasound signal being transmitted, based on the changed parameter. According to an exemplary embodiment, the ultrasound system 300 may change, based on the user input whose reception is determined in operation S840, positions of an aperture and a pulsed Doppler line being used for acquiring Doppler information at a sample volume.

According to an exemplary embodiment, after displaying the visual indicator indicating that the flow noise signal has been detected at the phantom gate in operation S830, the ultrasound system 300 may automatically perform operation S850 to change a parameter related to transmission of an ultrasound signal without determining whether the user input is received. For example, after displaying the visual indicator indicating that the flow noise signal has been detected at the phantom gate in operation S830, the ultrasound system 300 may automatically adjust a PRF to prevent generation of a phantom gate at a region where the flow noise signal has been detected. According to another exemplary embodiment, the ultrasound system 300 may change positions of an aperture and a pulsed Doppler line used for acquiring Doppler information at a sample volume to prevent generation of a phantom at a region where the flow noise signal has been detected, According to another exemplary embodiment, when the ultrasound system 300 determines that the flow noise signal is detected in operation S820, the ultrasound system 300 may automatically perform operation S850 of changing a parameter related to transmission of an ultrasound signal so that a flow noise signal may not be detected without performing operation S830 of displaying the visual indicator indicating that the flow noise signal has been detected or operation S840 of receiving a user input related to control of a flow noise signal.

Subsequently, the ultrasound system 300 may perform operation S810 again based on the parameter changed in operation S850.

Figure 9:
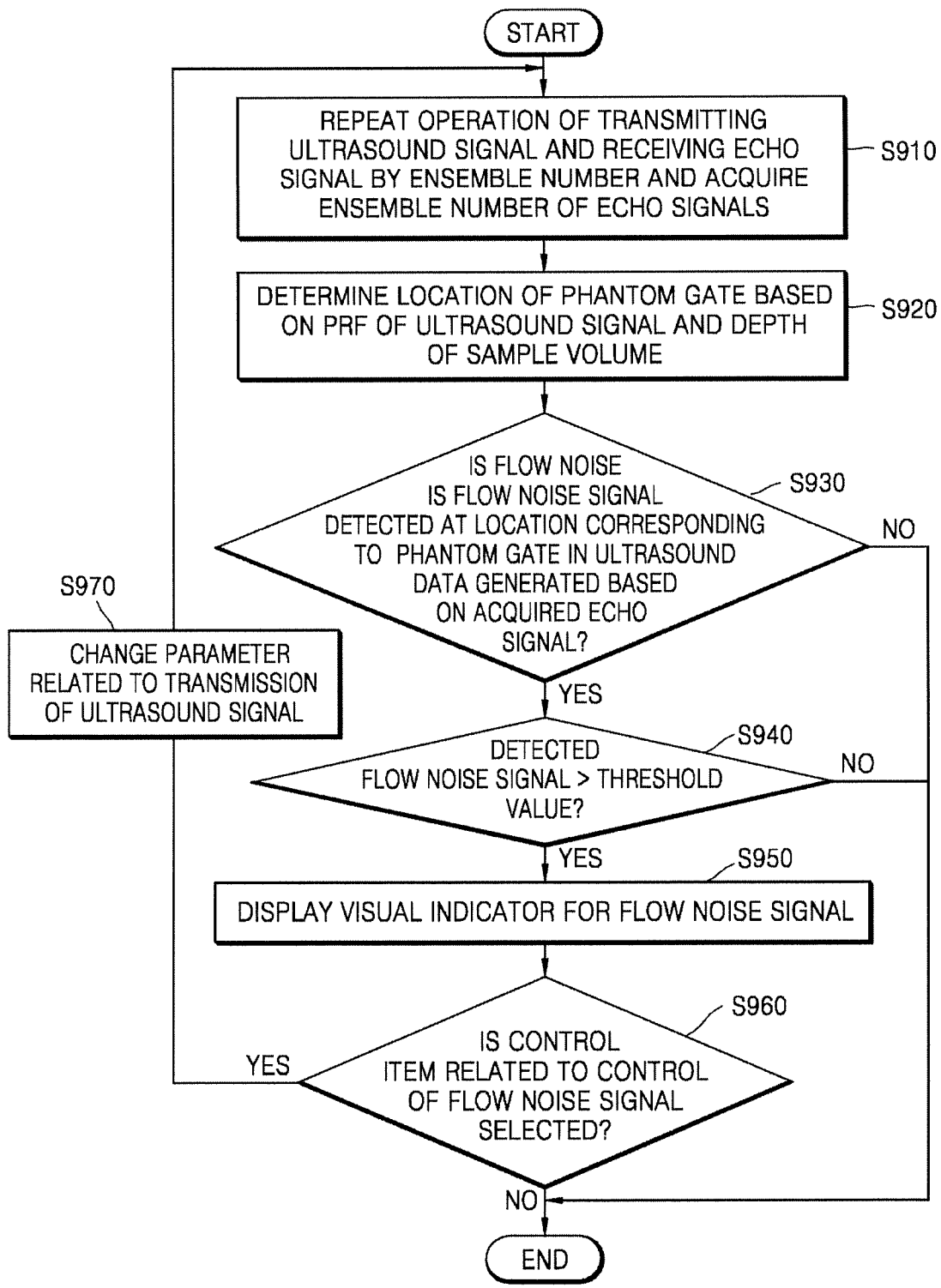
FIG. 9 is a flowchart of a method of providing a guide for a HPRF Doppler image according to another exemplary embodiment.

FIG. 9 is a flowchart of a method of providing a guide for a HPRF Doppler image, according to another exemplary embodiment. FIG. 9 may include more detailed exemplary embodiments for at least one operation in the method of FIG. 8.

The ultrasound system 300 transmits an ultrasound signal having a first PRF to an object including a sample volume and receives an echo signal from the sample volume and at least one phantom gate (S910). In this case, the ultrasound system 300 may transmit the ultrasound signal along a pulsed Doppler line passing through the sample volume.

According to an exemplary embodiment, the ultrasound system 300 initially transmits an ultrasound signal having a first PRF and receives an echo signal from a sample volume and at least one phantom gate in response to the initially transmitted ultrasound signal. According to an exemplary embodiment, after receiving the echo signal in response to the initially transmitted ultrasound signal, the ultrasound system 300 secondarily transmits the same ultrasound signal as the ultrasound signal having the first PRF and receives an echo signal from the sample volume and at least one phantom gate in response to the secondarily transmitted ultrasound signal. The ultrasound system 300 repeats an operation of transmitting an ultrasound signal and receiving an echo signal by an ensemble number.

The ultrasound system 300 determines a location of a phantom gate based on a PRF of an ultrasound signal and a depth of the sample volume (S920). The ultrasound signal transmitted in operation S910 is an ultrasound signal that is transmitted by an ensemble number to acquire Doppler information at the sample volume or phantom gate as well as at many other positions on a pulsed Doppler line. The ultrasound signal described in relation to operation S920 is an ultrasound signal that is transmitted to acquire more accurate Doppler information particularly at the sample volume. Thus, the ultrasound signal transmitted in operation S910 may not necessarily have the same ultrasound frequency or PRF as the ultrasound signal used in operation S920. However, the ultrasound signals in operation S910 and S920 may have the same ultrasound frequency or PRF when necessary.

In addition, although FIG. 9 shows that the ultrasound system 300 sequentially performs operations S910 and S920, the ultrasound system 300 may perform operation S920 prior to or simultaneously with operation S910 according to an exemplary embodiment.

The ultrasound system 300 determines whether a flow noise signal is present at a location corresponding to the phantom gate by analyzing ultrasound data generated based on the received echo signal (S930). In any one of operations S910, S920, and S930, the ultrasound system 300 may generate ultrasound data by using an echo signal. According to an exemplary embodiment, the ultrasound system 300 may determine the presence of a flow noise signal by analyzing ultrasound data at the location corresponding to the phantom gate from among the generated ultrasound data.

According to an exemplary embodiment, to detect a flow noise signal at a phantom gate, the ultrasound system 300 may analyze ultrasound data by using a predetermined algorithm. The predetermined algorithm may be at least one of Auto-correlation, Cross-correlation, Fast Fourier Transform, and Phase Locked Loop.

When the flow noise signal is not detected at the phantom gate in operation S930, the ultrasound system 300 terminates a method of providing a guide for a HPRF Doppler image. On the other hand, when the flow noise signal is detected at the phantom gate, the ultrasound system 300 performs operation S940.

The ultrasound system 300 compares a magnitude of the detected flow noise signal with a predetermined threshold value (S940). When the magnitude of the detected flow noise signal is less than the predetermined threshold value, the ultrasound system 300 terminates a method of providing a guide for a HPRF Doppler image. In this case, terminating the method of providing a guide for a HPRF Doppler image means that the ultrasound system 300 displays an ultrasound image of the object but does not display a visual indicator indicating that the flow noise signal has been detected at the phantom gate. According to an exemplary embodiment, when the flow noise signal is not detected at the phantom gate, i.e., when the ultrasound system 300 determines that the flow noise signal is not present in the phantom gate, the ultrasound system 300 may display a visual indicator indicating that the flow noise signal has not been detected at the phantom gate, together with an ultrasound image of the object. In this case, the visual indicator may include a message indicating that the flow noise signal has not been detected.

When the magnitude of the detected flow noise signal is greater than the predetermined threshold value in operation S940, the ultrasound system 300 performs operation S950.

The ultrasound system 300 displays a visual indicator indicating that the flow noise signal has been detected at the phantom gate (S950). Since displaying of the visual indicator has been described with reference to FIG. 8, a detailed description thereof will be omitted here.

Subsequently, the ultrasound system 300 performs operations S960 and S970. Since operations S960 and S970 respectively correspond to operations S840 and S850 described with reference to FIG. 8, detailed descriptions thereof will be omitted here.

While one or more embodiments have been described with reference to the figures, it will be understood by those of ordinary skill in the art that various changes in form and details may be made therein without departing from the spirit and scope of the inventive concept as defined by the following claims. Thus, it should be understood that the exemplary embodiments described therein should be considered in a descriptive sense only and not for purposes of limitation. The scope of the present inventive concept is defined not by the detailed description thereof but by the appended claims, and all differences within the scope of the appended claims and their equivalents will be construed as being included in the present inventive concept.

What is claimed is:

1. An ultrasound system comprising:
    an ultrasound transceiver configured to transmit ultrasound signals to an object including a sample volume and receive echo signals from the sample volume and at least one phantom gate that is generated corresponding to the sample volume;

a processor configured to generate an ultrasound image based on the received echo signals; and a display configured to display the generated ultrasound image, wherein the processor detects a flow noise signal at a first phantom gate among the at least one phantom gate by using the echo signals and controls the display to display a visual indicator representing the detected flow noise signal, wherein the processor changes a number of phantom gates generated and each location of additional phantom gates by adjusting a pulse repetition frequency (PRF), wherein the each location of additional phantom gates is different from a location of the first phantom gate, wherein the first phantom gate is generated to be positioned on a same line as the sample volume in a first pulsed Doppler line formed by a first aperture to transmit an ultrasound signal, wherein the processor performs an operation of changing the first aperture to a second aperture, adjacent to the first aperture, when the flow noise signal is detected in an echo signal of the first phantom gate, and wherein the second aperture forms a second pulsed Doppler line, and the second pulsed Doppler line passes through the sample volume but does not pass through a position corresponding to the first phantom gate.

2. The ultrasound system of claim 1, wherein the processor controls the ultrasound transceiver to repeat, by a predetermined ensemble number, an operation of transmitting the ultrasound signals along a pulsed Doppler line passing through the sample volume and receiving the echo signals from the sample volume and the at least one phantom gate, and wherein the predetermined ensemble number of the received echo signals comprise echo signals reflected from a plurality of positions included in the pulsed Doppler line.

3. The ultrasound system of claim 2, wherein the processor analyzes ultrasound data corresponding to a position of the at least one phantom gate from among ultrasound data generated based on the received echo signals reflected from the plurality of positions and detects the flow noise signal at the first phantom gate based on a result of the analyzing.

4. The ultrasound system of claim 1, wherein the ultrasound transceiver transmits the ultrasound signals by using an aperture in a maximum aperture and receives some of the echo signals by using another aperture that is different from the aperture in the maximum aperture, and wherein the processor detects the flow noise signal at the at least one phantom gate based on the some echo signals received using the another aperture.

5. The ultrasound system of claim 4, wherein the processor controls, based on a point where the aperture is located relative to the maximum aperture, the another aperture to be located at a point not overlapping the point where the aperture is located.

6. The ultrasound system of claim 1, wherein, to detect the flow noise signal, the processor uses at least one algorithm from among Auto-correlation, Cross-correlation, Fast Fourier Transform, and Phase Locked Loop to analyze the echo signals.

7. The ultrasound system of claim 1, wherein the processor controls the display to display the visual indicator only when a magnitude of the detected flow noise signal is greater than or equal to a predetermined threshold value.

8. The ultrasound system of claim 1, wherein the visual indicator comprises a message indicating that the flow noise signal has been detected at the at least one phantom gate.

9. The ultrasound system of claim 1, wherein the processor controls the visual indicator to be displayed at each position of the at least one phantom gate where the flow noise signal has been detected in such a manner that each position of the at least one phantom gate is distinguished from neighboring regions.

10. The ultrasound system of claim 1, further comprising a user interface device including a plurality of control items for changing parameters related to transmission of the ultrasound signals, wherein the processor controls the user interface device to display at least one control item related to control of the detected flow noise signal from among the plurality of control items.

11. The ultrasound system of claim 10, wherein the display is a touch screen comprising the user interface device.

12. The ultrasound system of claim 1, further comprising a user interface device, wherein, to avoid the detected flow noise signal, the processor changes, based on a user input via the user interface device, the pulse repetition frequency (PRF) of the transmitted ultrasound signals or changes an aperture being used to transmit the ultrasound signals.

13. A method of displaying an ultrasound image, the method comprising:

transmitting ultrasound signals to an object including a sample volume and receiving echo signals from the sample volume and at least one phantom gate that is generated corresponding to the sample volume;

generating the ultrasound image based on the received echo signals; and detecting a flow noise signal at a first phantom gate among the at least one phantom gate by using the echo signals;

displaying a visual indicator representing the detected flow noise signal together with the generated ultrasound image; and acquiring Doppler information at the sample volume by performing an operation of changing a number of phantom gates generated and each location of additional phantom gates by adjusting a pulse repetition frequency (PRF), wherein the each location of the phantom gates is different from a location of the first phantom gate, wherein the first phantom gate is generated to be positioned on a same line as the sample volume in a first pulsed Doppler line formed by a first aperture to transmit an ultrasound signal, wherein the processor performs an operation of changing the first aperture to a second aperture, adjacent to the first aperture, when the flow noise signal is detected in an echo signal of the first phantom gate, and wherein the second aperture forms a second pulsed Doppler line, and the second pulsed Doppler line passes through the sample volume but does not pass through a position corresponding to the first phantom gate.

14. The method of claim 13, wherein the transmitting of the ultrasound signals and the receiving of the echo signals comprises repeating, by a predetermined ensemble number, an operation of transmitting the ultrasound signals along a pulsed Doppler line passing through the sample volume and receiving the echo signals from the sample volume and the at least one phantom gate, and wherein the predetermined ensemble number of the received echo signals comprise echo signals reflected from a plurality of positions included in the pulsed Doppler line.

15. The method of claim 14, wherein the detecting of the flow noise signal comprises analyzing ultrasound data corresponding to a position of the at least one phantom gate from among ultrasound data generated based on the received echo signals reflected from the plurality of positions and detecting the flow noise signal at the first phantom gate based on a result of the analyzing.

16. The method of claim 13, wherein the ultrasound signals are transmitted by using an aperture in a maximum aperture, and some of the echo signals are received by using another aperture that is different from the aperture in the maximum aperture, and wherein the flow noise signal is detected at the at least one phantom gate based on the some echo signals received using the another aperture.

17. The method of claim 16, wherein a point where the another aperture is located is determined based on a point where the aperture is located relative to the maximum aperture.

18. The method of claim 13, wherein the flow noise signal is detected by analyzing the echo signals by using at least one algorithm from among Auto-correlation, Cross-correlation, Fast Fourier Transform, and Phase Locked Loop.

19. The method of claim 13, wherein the visual indicator is displayed only when a magnitude of the detected flow noise signal is greater than or equal to a predetermined threshold value.

20. The method of claim 13, wherein the visual indicator comprises a message indicating that the flow noise signal has been detected at the at least one phantom gate.

21. The method of claim 13, wherein the visual indicator is displayed at each position of the at least one phantom gate where the flow noise signal has been detected so that each position of the at least one phantom gate is distinguished from neighboring regions.

22. The method of claim 13, wherein the visual indicator is displayed at a position corresponding to at least one control item related to control of the detected flow noise signal in a user interface device comprising a plurality of control items for changing parameters related to transmission of the ultrasound signals.

23. The method of claim 13, further comprising, to avoid the detected flow noise signal, changing the pulse repetition frequency (PRF) of the transmitted ultrasound signals or an aperture being used to transmit the ultrasound signals based on a user input via a user interface device.

24. A non-transitory computer-readable recording medium having recorded thereon a program for executing the method of claim 13.

* * * * *